United States Patent
Cheng et al.

(10) Patent No.: US 11,961,231 B2
(45) Date of Patent: Apr. 16, 2024

(54) METHOD AND SYSTEM FOR MEDICAL IMAGE INTERPRETATION

(71) Applicant: Acer Incorporated, New Taipei (TW)

(72) Inventors: Meng-Che Cheng, New Taipei (TW); Ming-Tzuo Yin, New Taipei (TW)

(73) Assignee: Acer Incorporated, New Taipei (TW)

( * ) Notice: Subject to any disclaimer, the term of this patent is extended or adjusted under 35 U.S.C. 154(b) by 420 days.

(21) Appl. No.: 17/357,994

(22) Filed: Jun. 25, 2021

(65) Prior Publication Data
US 2022/0383490 A1    Dec. 1, 2022

(30) Foreign Application Priority Data

May 27, 2021 (TW) .................... 110119273

(51) Int. Cl.
*G06T 7/00* (2017.01)
*G06F 18/213* (2023.01)
*G06F 18/241* (2023.01)
*G06N 3/08* (2023.01)
*G16H 30/20* (2018.01)
*G16H 50/20* (2018.01)

(52) U.S. Cl.
CPC .......... *G06T 7/0012* (2013.01); *G06F 18/213* (2023.01); *G06F 18/241* (2023.01); *G06N 3/08* (2013.01); *G16H 30/20* (2018.01); *G16H 50/20* (2018.01); *G06T 2207/20081* (2013.01); *G06T 2207/20084* (2013.01); *G06T 2207/30004* (2013.01)

(58) Field of Classification Search
None
See application file for complete search history.

(56) References Cited

U.S. PATENT DOCUMENTS

2020/0104996 A1* 4/2020 Akahori ................. G16H 50/20

FOREIGN PATENT DOCUMENTS

| CN | 106934798 | 7/2017 |
| TW | 201942868 | 11/2019 |
| WO | 2019232027 | 12/2019 |

OTHER PUBLICATIONS

"Search Report of Europe Counterpart Application", dated Jan. 14, 2022, p. 1-p. 10.
Zhang Tianfu et al., "Deep Learning Feature Fusion-Based Retina Image Classification", Laser & Optoelectronics Progres, with English abstract, Dec. 2020, pp. 241025-1-241025-8., vol. 57.
Wang Chong et al., "Automatic Classification of Retinal Optical Coherence Tomography Images via Convolutional Neural Networks with Joint Decision", Chinese Journal of Biomedical Engineering, with English abstract, Dec. 2018, pp. 1-8., vol. 37.

* cited by examiner

*Primary Examiner* — Leon Flores
(74) *Attorney, Agent, or Firm* — JCIPRNET

(57) ABSTRACT

A method and a system for medical image interpretation are provided. A medical image is provided to a convolutional neural network model. The convolutional neural network model includes a feature extraction part, a first classifier, and N second classifiers. N feature maps are generated by using the last layer of the feature extraction part of the convolutional neural network model. N symptom interpretation results of N symptoms of a disease are obtained based on the N feature maps through the N second classifiers. A disease interpretation result of the disease is obtained based on the N feature maps through the first classifier.

20 Claims, 4 Drawing Sheets

METHOD AND SYSTEM FOR MEDICAL IMAGE INTERPRETATION

CROSS-REFERENCE TO RELATED APPLICATION

This application claims the priority benefit of Taiwan application serial no. 110119273, filed on May 27, 2021. The entirety of the above-mentioned patent application is hereby incorporated by reference herein and made a part of this specification.

BACKGROUND

Technical Field

The disclosure relates to medical image interpretation, and more particularly to a method and a system for medical image interpretation based on deep learning.

Description of Related Art

As deep learning becomes well-developed, artificial intelligence is increasingly used to assist medical image interpretation. However, artificial intelligence models having high accuracy are often relatively complicated, with their decision-making logic or determination basis too difficult to understand. In other words, the artificial intelligence models are unable to explain reasons behind their decisions and actions to human beings, which may affect reliability of the artificial intelligence models. In particular, in the field of medical diagnosis with assistance of artificial intelligence models, decision-making rationality and transparency are of utmost importance.

In this regard, a series of explainable AI (as known as XAI) methods have been proposed to be the focus of research. These methods try to interpret how artificial intelligence models make decisions. At present, most of the explainable AI methods may only present importance and location of features in input data, and are unable to further explain the features, so it cannot provide any valuable explanation for medical personnel. More specifically, even if the explainable AI method may present relevant information about the important features in the input data, medical personnel still cannot determine whether the features that the artificial intelligence model focuses on is the symptoms of a specific disease. Therefore, the information cannot serve as the basis for interpretation confidence improvement or further explanation.

SUMMARY

The disclosure provides a method and a system for medical image interpretation, where a convolutional neural network model may provide both symptom interpretation information and disease interpretation information, making the method and the system closer to actual requirements of medical personnel.

An embodiment of the disclosure provides a method for medical image interpretation, adapted for a computer device, and including the following steps. A medical image is provided to a convolutional neural network model, where the convolutional neural network model includes a feature extraction part, a first classifier, and N second classifiers. N feature maps are generated by using a last layer of the feature extraction part of the convolutional neural network model. N symptom interpretation results of N symptoms of a disease are obtained based on the N feature maps through the N second classifiers. A disease interpretation result of the disease is obtained based on the N feature maps through the first classifier.

An embodiment of the disclosure provides a system for medical image interpretation, including a storage device and a processor. The processor is connected to the storage device and is configured to perform the following steps. A medical image is provided to a convolutional neural network model, where the convolutional neural network model includes a feature extraction part, a first classifier, and N second classifiers. N feature maps are generated by using a last layer of the feature extraction part of the convolutional neural network model. N symptom interpretation results of N symptoms of a disease are obtained based on the N feature maps through the N second classifiers. A disease interpretation result of the disease is obtained based on the N feature maps through the first classifier.

In order to make the above-mentioned features and advantages of the present invention more comprehensible, the following specific embodiments are described in detail in conjunction with the accompanying drawings.

DESCRIPTION OF THE EMBODIMENTS

Figure 1:
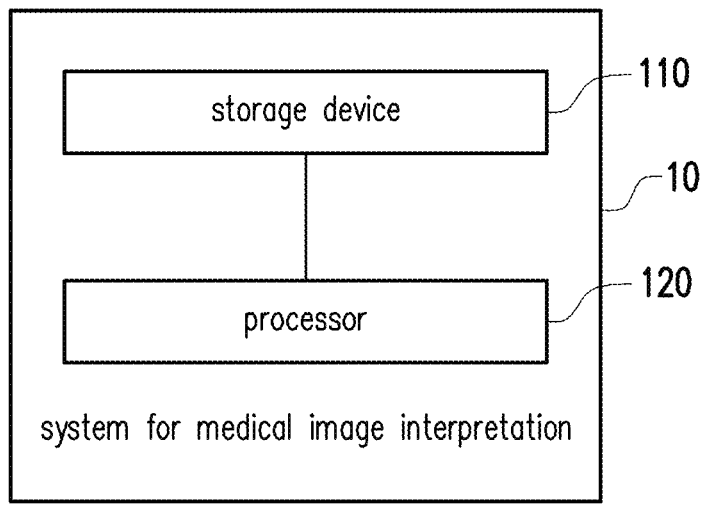
FIG. 1 is a schematic diagram of a system for medical image interpretation according to an embodiment of the disclosure.

Part of the embodiments of the disclosure will be described in detail below with accompanying drawings. For reference numerals used in the following description, the same reference numerals appearing in different drawings will be regarded as the same or similar elements. These embodiments are only a part of the disclosure and do not disclose all possible implementations of the disclosure. More precisely, these embodiments only serve as examples of the system and the method as recited in the claims of the disclosure.

FIG. 1 is a schematic diagram of a system for medical image interpretation according to an embodiment of the disclosure. However, it is only for ease of description, and is not intended to limit the disclosure. With reference to FIG. 1, a system 10 for medical image interpretation includes a storage device 110 and a processor 120. In some embodiments, the system 10 for medical image interpretation may be implemented as a notebook computer, a desktop computer, a tablet computer, an industrial computer, a server, or other types of computer devices, and the disclosure is not limited thereto.

The storage device 110 is used to store images, instructions, program codes, software modules, or other data. The storage device 110 may include a volatile storage circuit and a non-volatile storage circuit. The volatile storage circuit is used to store data in a volatile manner. For example, the volatile storage circuit may include a random access memory (RAM) or a similar volatile storage medium. The non-volatile storage circuit is used to store data in a non-volatile manner. For example, the non-volatile storage circuit may include a read only memory (ROM), a solid state disk (SSD), and/or a traditional hard disk drive (HDD) or a similar non-volatile storage medium.

The processor 120 is coupled to the storage device 110 to control the entire or part of operation of the system 10 for medical image interpretation. The processor 120 is, for example, a central processing unit (CPU) or other programmable general-purpose or special-purpose microprocessor, a digital signal processor (DSP), a programmable controller, an application specific integrated circuit (ASIC), a programmable logic device (PLD), a graphics processing unit (GPU), or other similar device or a combination of these devices. The processor 120 may execute the program codes, software modules, instructions, and the like recorded in the storage device 110 to implement the method for medical image interpretation in the embodiments of the disclosure.

Figure 2:
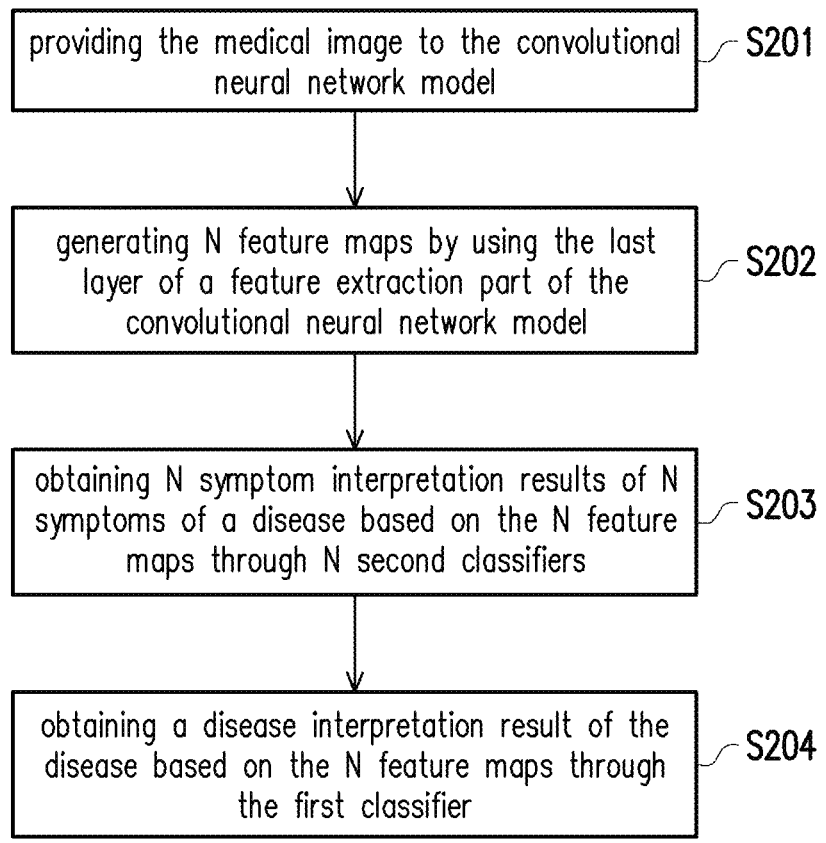
FIG. 2 is a flowchart of a method for medical image interpretation according to an embodiment of the disclosure.

FIG. 2 is a flowchart of a method for medical image interpretation according to an embodiment of the disclosure. With reference to FIG. 2, the method of this embodiment is adapted for the system 10 for medical image interpretation in the above embodiment. Detailed steps of this embodiment are described as follows with reference to elements of the system 10 for medical image interpretation.

In the embodiments of the disclosure, a convolutional neural network model may assist medical personnel in interpreting a medical image; that is, the convolutional neural network model may assess presence or severity of a disease of a patient based on the medical image. Generally speaking, when using a medical image for disease diagnosis, medical personnel determines the presence and severity of a certain disease of a patient according to multiple symptoms in the medical image. Based on this, in the embodiments of the disclosure, the convolutional neural network model not only provides a disease interpretation result but also assesses the presence or severity of N symptoms of a certain disease in the medical image. Taking retinopathy as an example for the disease, the symptoms mentioned above may be, for example, hemorrhage or angiogenesis.

In step S201, the processor 120 provides the medical image to the convolutional neural network model. The medical image may include an X-ray image, an ultrasound image, a computed tomography (CT) image, a magnetic resonance imaging (MRI) image, a pathological slice image, or other captured image of the patient for medical diagnosis. For example, the medical image may be a fundus image captured through a funduscope.

In an embodiment, the convolutional neural network model is constructed in advance based on a training dataset for deep learning, and model parameters of the convolutional neural network model (such as weight information, the number of convolutional kernels, and the number of network layers) have been determined by prior training and may be recorded in the storage device 110. The processor 120 may input the medical image to the convolutional neural network model, and the convolutional neural network model may output a disease interpretation result of the patient in response to the medical image. The disease interpretation result includes disease classification information of a disease. For example, the convolutional neural network model may assess severity of a certain disease as grade 0 (not sick), grade 1, grade 2, or grade 3 based on the medical image. In addition, in an embodiment, the convolutional neural network model may further output N symptom interpretation results of N symptoms of a disease according to the medical image. The N symptom interpretation results respectively include symptom presence information or symptom classification information of one of the N symptoms. For example, assuming that a certain disease has N symptoms, the convolutional neural network model may assess the severity of these symptoms as grade 0 (not existing), grade 1, grade 2, or grade 3 based on the medical image. The symptom presence information serves as an interpretation result of whether the symptom exists.

In step S202, the processor 120 generates N feature maps by using the last layer of a feature extraction part of the convolutional neural network model. In detail, in an embodiment, the convolutional neural network model may include the feature extraction part and a first classifier. The feature extraction part of the convolutional neural network model is used to perform convolutional computation processing to the medical image for extracting features of the medical image and thereby generating the feature maps (or called feature vectors). In following, these feature maps are fed into the first classifier, so that the first classifier outputs the disease interpretation result of a certain disease.

In an embodiment, the feature extraction part may include at least one convolutional layer. In an embodiment, the feature extraction part may include at least one convolutional layer and at least one pooling layer. In an embodiment, the feature extraction part of the convolutional neural network model includes multiple layers sequentially connected in series. These layers may include at least one convolutional layer and at least one pooling layer. Each layer in the feature extraction part of the convolutional neural network model may receive and input the medical image or the feature maps generated by the previous layer for executing relative computation processing to generate and output the feature maps. The convolutional layer in the feature extraction part may generate the feature maps by performing convolutional computation according to one or more convolutional kernels. The number of the feature maps output by each convolutional layer depends on the number of the convolutional kernels used by the convolutional layer. The convolutional kernels may slide on the feature maps by a fixed step length. Whenever the convolutional kernels are shifted, each weight included in the convolutional kernels is multiplied by and then added with all feature values of an overlapping area on the feature maps. On the other hand, the pooling layer may downsample the feature maps to obtain lower-dimension feature maps.

It should be noted that in the embodiments of the disclosure, the number of the feature maps output by the last layer of the feature extraction part of the convolutional neural network model is consistent with the number of the symptoms. In an embodiment, the last layer of the feature extraction part of the convolutional neural network model is a convolutional layer or a pooling layer. That is, assuming that a certain disease has N types of the symptoms observable in the medical image, the number of the feature maps output by the last layer of the feature extraction part is N as well, and N is an integer greater than 0. In light of this, in the embodiments of the disclosure, the number of the convolutional kernels used in the last convolutional layer in the feature extraction part of the convolutional neural network model depends on the number of the symptoms.

Figure 3:
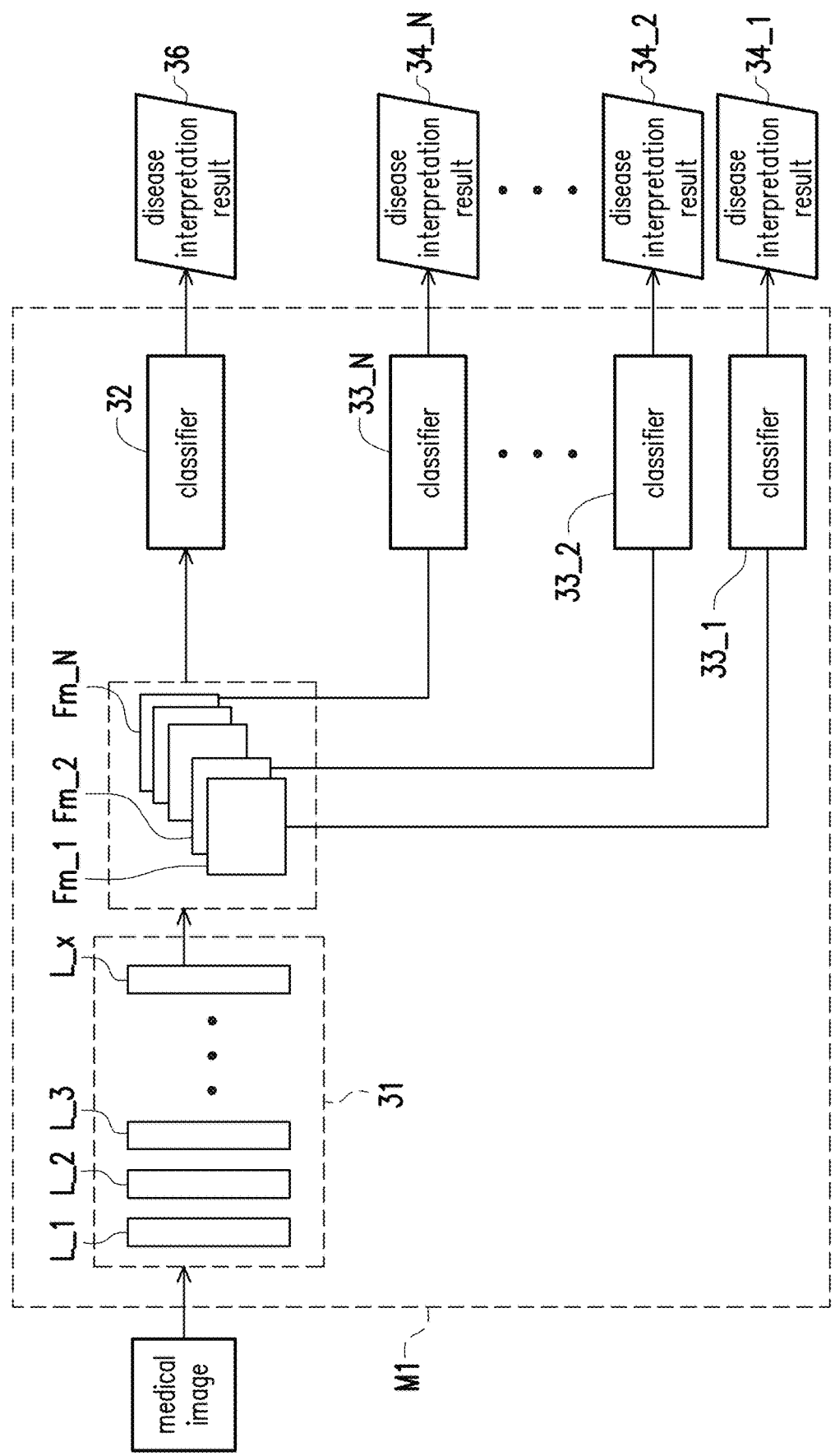
FIG. 3 is a schematic diagram of a convolutional neural network model according to an embodiment of the disclosure.

For example, FIG. 3 is a schematic diagram of a convolutional neural network model according to an embodiment of the disclosure. With reference to FIG. 3, a convolutional neural network model M1 may include a feature extraction part 31 and a classifier 32 (i.e. the first classifier). The feature extraction part 31 includes multiple layers L_1 to L_x connected in series with each other, and the last layer L_x in the feature extraction part 31 may be a convolutional layer or a pooling layer. The last layer L_x of the feature extraction part 31 outputs N feature maps Fm_1 to Fm_N.

Next, in step S203, the processor 120 obtains N symptom interpretation results of N symptoms of a disease based on the N feature maps through N second classifiers. In more detail, in addition to the feature extraction part and the first classifier, the convolutional neural network model further includes the N second classifiers. Here, the N second classifiers respectively output one of the N symptom interpretation results according to one of the N feature maps. In an embodiment, the processor 120 may input the N feature maps to the corresponding second classifiers in a one-to-one manner so that the second classifiers respectively output one of the N symptom interpretation results in response to receiving one of the N feature maps. In other words, each second classifier may identify the symptoms and the severity thereof in the medical image according to a corresponding one of the feature maps, thereby outputting the corresponding symptom interpretation result respectively.

For example, with reference to FIG. 3 again, the convolutional neural network model M1 may further include N classifiers 33_1 to 33_N (i.e. the second classifiers). The classifier 33_1 outputs a symptom interpretation result 34_1 related to a symptom of a disease according to the feature map Fm_1. The classifier 33_2 outputs a symptom interpretation result 34_2 related to another symptom of the disease according to the feature map Fm_2. In the same way, the N classifiers 33_1 to 33_N of the convolutional neural network model M1 may output N symptom interpretation results 34_1~34_N related to N symptoms.

In addition, in step S204, the processor 120 obtains a disease interpretation result of the disease based on the N feature maps through the first classifier. In an embodiment, the processor 120 may feed the N feature maps into the first classifier. The first classifier may determine the presence and/or severity of the disease in the patient according to the N feature maps, thereby outputting a disease interpretation result 36. For example, with reference to FIG. 3 again, the classifier 32 (i.e. the first classifier) may receive the N feature maps Fm_1 to Fm_N to output the disease interpretation result 36.

In an embodiment, classification functions of the first classifier and the N second classifiers may be implemented by at least one fully connected layer, respectively. That is, the first classifier includes at least one fully connected layer, and each of the N second classifiers includes at least one fully connected layer. In detail, the processor 120 may generate a one-dimensional vector according to the N feature maps and feed the one-dimensional vector into the at least one fully connected layer in the first classifier for classification, thereby obtaining the disease interpretation result. In addition, the processor 120 may respectively generate a one-dimensional vector according to one of the N feature maps and feed the one-dimensional vector into the at least one fully connected layer in a corresponding one of the second classifiers for classification, thereby obtaining one of the N symptom interpretation results.

In addition, in one embodiment, before actually using the trained convolutional neural network model, it is necessary to train the convolutional neural network model with training data, and these training data include a large number of labeled training medical images. In an embodiment, during a training phase of the convolutional neural network model, the processor 120 may synchronously train the feature extraction part, the first classifier, and the N second classifiers in the convolutional neural network model based on an overall loss function. The processor 120 may adjust weight information in the convolutional neural network model by backpropagation from back to front according to loss values output by the overall loss function, such as the weight information in the convolutional kernels and the weight information of the fully connected layers.

In an embodiment, the convolutional neural network model performs backpropagation training based on the overall loss function. This overall loss function includes a weighted sum of (N+1) loss values of (N+1) loss functions, and N loss functions among the (N+1) loss functions respectively correspond to the N second classifiers. The remaining one among the (N+1) loss functions corresponds to the first classifier. These loss functions are, for example, mean square error (MSE) loss functions, mean absolute error (MAE) loss functions, Softmax loss functions, or the like. In detail, each symptom classification operation and disease classification operation uses the loss functions independent from each other, and an overall loss value generated by the overall loss function is the weighted sum of the (N+1) loss values of the (N+1) loss functions independent from each other.

For example, when the processor 120 inputs a certain labeled training medical image to the convolutional neural network model, the convolutional neural network model may generate a disease interpretation result and N symptom interpretation results according to current weight information. By inputting the above disease interpretation result, the N symptom interpretation results, and real label information to the overall loss function, the processor 120 may obtain an overall loss value and update the weight information in the convolutional neural network model by backpropagation. The processor 120 inputs the disease interpretation result and the corresponding real label information to the loss function corresponding to the first classifier to obtain a loss value. In addition, the processor 120 further inputs each symptom interpretation result and the corresponding real label information to a loss function corresponding to the second classifiers to obtain multiple loss values respectively related to multiple symptoms. In following, by weighting and calculating the above (N+1) loss values, the processor 120 may obtain the overall loss value.

Based on the architecture of the convolutional neural network model and the design of the loss functions, the convolutional neural network model in the embodiments of the disclosure may be optimized towards the disease interpretation result, and this optimization direction is generated according to reasonable features of the symptoms. That is, the convolutional neural network model makes decisions based on specific symptom conditions in the medical image to avoid unexpected deviations existing in the training medical image and reducing reliability of the convolutional neural network model.

Based on the foregoing description, in the embodiments of the disclosure, the processor 120 may obtain the disease interpretation result of a certain disease and the symptom interpretation results of multiple symptoms by inputting the medical image to the convolutional neural network model. The disease interpretation result and the symptom interpretation results may be displayed on a display device or be printed on paper for medical personnel's reference to provide auxiliary diagnosis information that better meets medical personnel's requirements.

In addition, in an embodiment, the processor 120 may input one of the N feature maps to one of the N second classifiers so that the one of the N second classifiers outputs one of the N symptom interpretation results. That is, the N feature maps may be directly input to the corresponding second classifiers respectively, so that the N second classifiers may respectively generate the N symptom interpretation results according to the N feature maps. Alternatively, in an embodiment, the convolutional neural network model may further include a symptom feature extraction part, and the symptom feature extraction part includes at least one convolutional layer. The processor 120 may input one of the N feature maps to the symptom feature extraction part to obtain at least one symptom feature map, and may input the at least one symptom feature map to one of the N second classifiers so that the one of the N second classifiers outputs one of the N symptom interpretation results. That is, the processor 120 may respectively perform convolutional computation processing to the N feature maps for feature extraction and then input feature extraction results to the corresponding second classifiers.

Figure 4A:
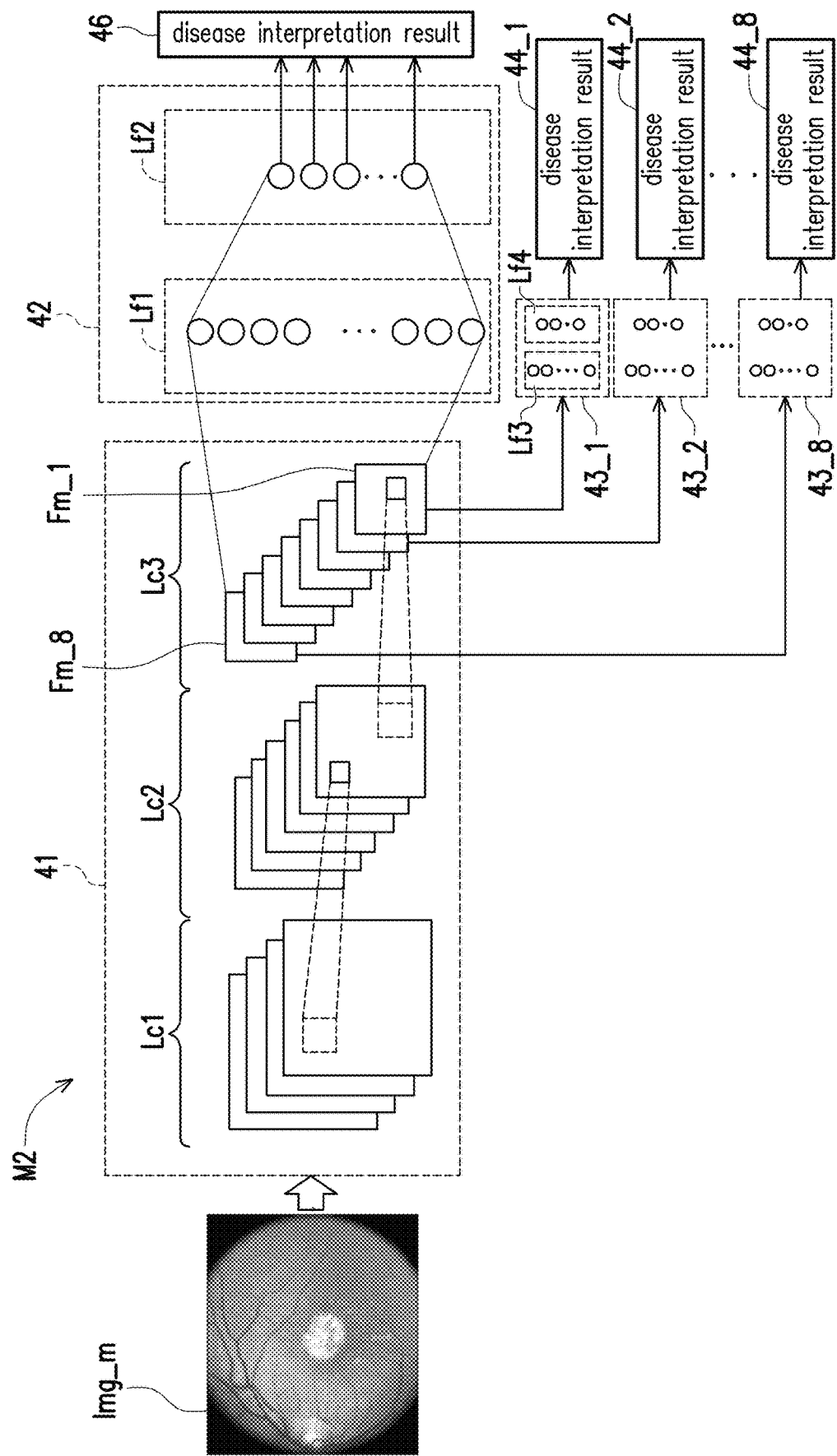
FIG. 4A and FIG. 4B are schematic diagrams of convolutional neural network models according to embodiments of the disclosure.
Figure 4B:
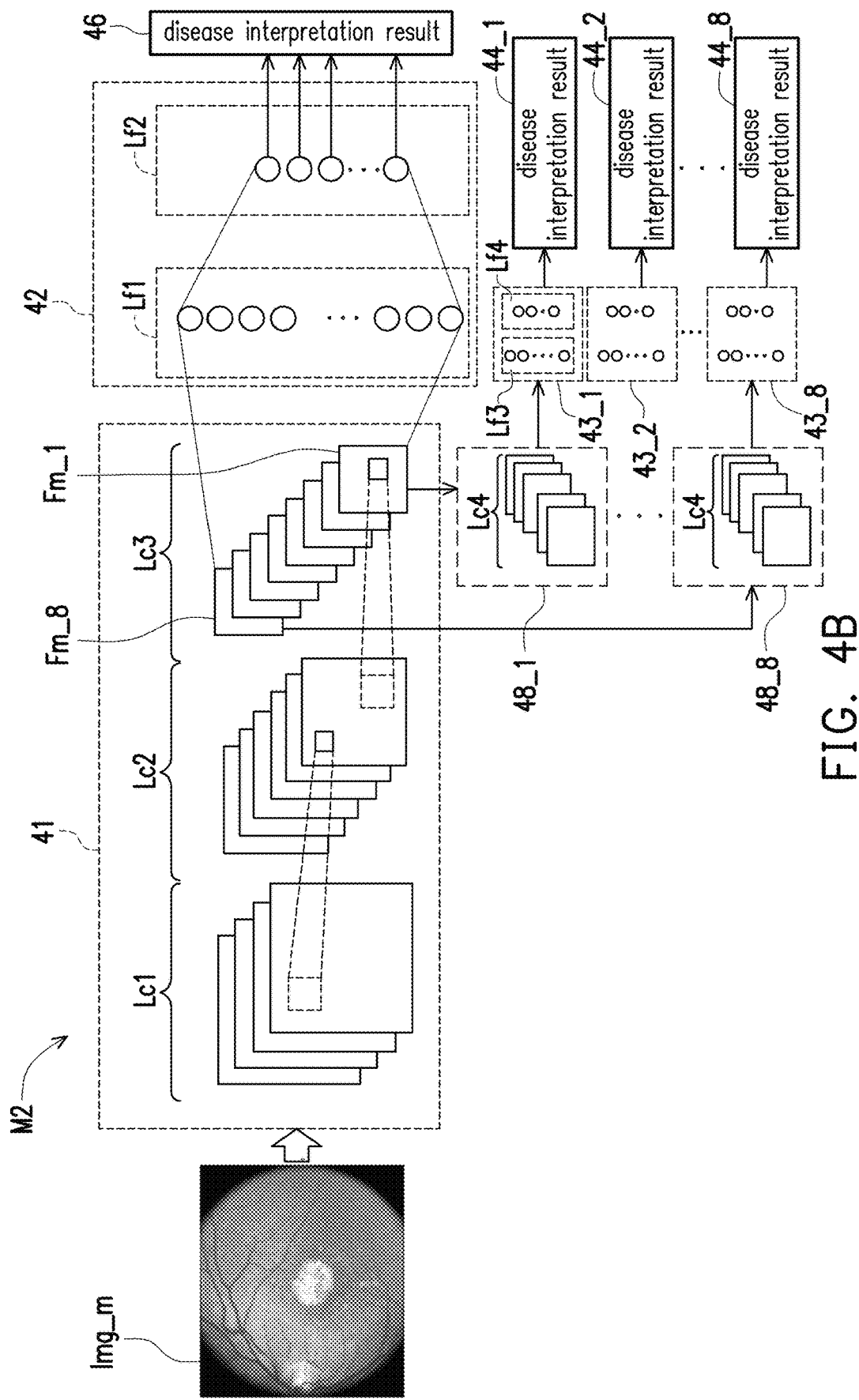

For convenience of description regarding the concept of the disclosure, a further description is provided below with reference to FIG. 4A and FIG. 4B. FIG. 4A and FIG. 4B are schematic diagrams of the convolutional neural network models according to the embodiments of the disclosure. As exemplified in FIG. 4A and FIG. 4B, it is assumed that the number of symptoms is eight, which means N=8.

With reference to FIG. 4A, the processor 120 may input a medical image Img_m to a convolutional neural network model M2. The convolutional neural network model M2 includes a feature extraction part 41 and a classifier 42. The feature extraction part 41 may include three convolutional layers Lc1 to Lc3. It should be noted that the convolutional layer Lc3, which is the last layer, generates eight feature maps Fm1_1 to Fm1_8 by using eight convolutional kernels. The eight feature maps Fm1_1 to Fm1_8 are fed into the classifier 42. The classifier 42 may include fully connected layers Lf1 and Lf2. The fully connected layer Lf1 may be referred to as a flat layer, and the fully connected layer Lf2 may be referred to as an output layer. The fully connected layer Lf2 may output a disease interpretation result 46. The disease interpretation result 46 may include disease classification information of a disease, such as the presence or severity of the disease of a patient. In addition, since the number of the symptoms is eight, the convolutional neural network model M2 further includes eight classifiers 43_1 to 43_8. The eight feature maps Fm1_1 to Fm1_8 may be respectively fed into the classifiers 43_1 to 43_8. The classifiers 43_1 to 43_8 may respectively include two fully connected layers (for example, the fully connected layers Lf3 and Lf4 of the classifier 43_1). The classifiers 43_1 to 43_8 may respectively generate symptom interpretation results 44_1 to 44_8 according to their corresponding feature maps Fm1_1 to Fm1_8. Based on this, the processor 120 may generate the disease interpretation result 46 and the symptom interpretation results 44_1 to 44_8 for medical personnel's reference by using the convolutional neural network model M2.

On the other hand, with reference to FIG. 4B, a convolutional neural network model M3, similar to the convolutional neural network model M2 in FIG. 4A, may include the feature extraction part 41, the classifier 42, and the eight classifiers 43_1 to 43_8. Different from the example in FIG. 4A, the convolutional neural network model M3 may further include symptom feature extraction parts 48_1 to 48_8 respectively connected with the classifiers 43_1 to 43_8. The symptom feature extraction parts 48_1 to 48_8 may respectively include a convolutional layer (for example, a convolutional layer Lc4 of the symptom feature extraction part 48_1). The symptom feature extraction parts 48_1 to 48_8 may respectively perform feature extraction to their corresponding feature maps Fm1_1 to Fm1_8 to generate multiple symptom feature maps. These symptom feature maps may be respectively input to the corresponding classifiers 43_1 to 43_8 so that the classifiers 43_1 to 43_8 may generate the symptom interpretation results 44_1 to 44_8 according to the corresponding symptom feature maps, respectively.

However, the examples in FIG. 4A and FIG. 4B are only used to describe the disclosure, and are not intended to limit the disclosure. The number of the fully connected layers in the classifiers may be designed according to actual requirements, and the number of the convolutional layers in the feature extraction parts and the symptom feature extraction parts may also be designed according to actual requirements.

In summary, in the embodiments of the disclosure, when medical personnel use the convolutional neural network model to assist medical image interpretation, the convolutional neural network model may not only provide the disease interpretation result of a disease but also provide the symptom interpretation results of multiple symptoms of the disease. Therefore, the medical personnel may clearly understand that the convolutional neural network model makes decision information about the disease based on the presence of these symptoms in the medical image and thereby improves the reliability of using the convolutional neural network model for medical image interpretation.

Although the disclosure has been described with reference to the above embodiments, they are not intended to limit the disclosure. It will be apparent to one of ordinary skill in the art that modifications to the described embodiments may be made without departing from the spirit and the scope of the disclosure. Accordingly, the scope of the disclosure will be defined by the attached claims and their equivalents and not by the above detailed descriptions.

What is claimed is:

1. A method for medical image interpretation, adapted for a computer device, the method comprising:
   providing a medical image to a convolutional neural network model, wherein the convolutional neural network model comprises a feature extraction part, a first classifier, and N second classifiers, wherein N is a positive integer;
   generating N feature maps by using the feature extraction part of the convolutional neural network model;
   obtaining N symptom interpretation results of N symptoms of a disease based on the N feature maps through the N second classifiers; and
   obtaining a disease interpretation result of the disease based on the N feature maps through the first classifier,
   wherein one of the N second classifiers outputs one of the N symptom interpretation results only according to part of the N feature maps, and another one of the N second classifiers outputs another of the N symptom interpretation results only according to another part of the N feature maps.

2. The method for medical image interpretation according to claim 1, wherein the N feature maps are generated by using a last layer of the feature extraction part of the convolutional neural network model, and the last layer is a convolutional layer or a pooling layer.

3. The method for medical image interpretation according to claim 1, wherein the feature extraction part of the convolutional neural network model comprises a plurality of layers sequentially connected in series, and the feature extraction part of the convolutional neural network model comprises at least one convolutional layer.

4. The method for medical image interpretation according to claim 3, wherein the feature extraction part of the convolutional neural network model further comprises at least one pooling layer.

5. The method for medical image interpretation according to claim 1, wherein the first classifier comprises at least one fully connected layer, and each of the N second classifiers comprises at least one fully connected layer.

6. The method for medical image interpretation according to claim 1, wherein the N symptom interpretation results respectively comprise symptom presence information or symptom classification information of one of the N symptoms.

7. The method for medical image interpretation according to claim 1, wherein the disease interpretation result comprises disease classification information of the disease.

8. The method for medical image interpretation according to claim 1, further comprising:
   training the convolutional neural network model, wherein the convolutional neural network model is trained based on an overall loss function, the overall loss function comprises a weighted sum of (N+1) loss values of (N+1) loss functions, N loss functions among the (N+1) loss functions correspond to the N second classifiers respectively, and a remaining one among the (N+1) loss functions corresponds to the first classifier.

9. The method for medical image interpretation according to claim 1, wherein a step of obtaining N symptom interpretation results of the N symptoms of the disease based on the N feature maps through the N second classifiers comprises:
   inputting one of the N feature maps to one of the N second classifiers so that the one of the N second classifiers outputs one of the N symptom interpretation results.

10. The method for medical image interpretation according to claim 1, wherein the convolutional neural network model further comprises a symptom feature extraction part, the symptom feature extraction part comprises at least one convolutional layer, and a step of obtaining N symptom interpretation results of the N symptoms of the disease based on the N feature maps through the N second classifiers comprises:
    inputting one of the N feature maps to the symptom feature extraction part for obtaining at least one symptom feature map; and
    inputting the at least one symptom feature map to one of the N second classifiers so that the one of the N second classifiers outputs one of the N symptom interpretation results.

11. A system for medical image interpretation, comprising:
    a storage device; and
    a processor, coupled to the storage device and configured to:
      provide a medical image to a convolutional neural network model, wherein the convolutional neural network model comprises a feature extraction part, a first classifier, and N second classifiers, wherein N is a positive integer;
      generate N feature maps by using the feature extraction part of the convolutional neural network model;
      obtain N symptom interpretation results of N symptoms of a disease based on the N feature maps through the N second classifiers; and
      obtain a disease interpretation result of the disease based on the N feature maps through the first classifier,
    wherein one of the N second classifiers outputs one of the N symptom interpretation results only according to part of the N feature maps, and another one of the N second classifiers outputs another of the N symptom interpretation results only according to another part of the N feature maps.

12. The system for medical image interpretation according to claim 11, wherein the N feature maps are generated by using a last layer of the feature extraction part of the convolutional neural network model, and the last layer is a convolutional layer or a pooling layer.

13. The system for medical image interpretation according to claim 11, wherein the feature extraction part of the convolutional neural network model comprises a plurality of layers sequentially connected in series, and the feature extraction part of the convolutional neural network model comprises at least one convolutional layer.

14. The system for medical image interpretation according to claim 13, wherein the feature extraction part of the convolutional neural network model further comprises at least one pooling layer.

15. The system for medical image interpretation according to claim 11, wherein the first classifier comprises at least one fully connected layer, and each of the N second classifiers comprises at least one fully connected layer.

16. The system for medical image interpretation according to claim 11, wherein the N symptom interpretation results respectively comprise symptom presence information or symptom classification information of one of the N symptoms.

17. The system for medical image interpretation according to claim 11, wherein the disease interpretation result comprises disease classification information of the disease.

18. The system for medical image interpretation according to claim 11, wherein the processor is further configured to:
    train the convolutional neural network model, wherein the convolutional neural network model is trained based on an overall loss function, the overall loss function comprises a weighted sum of (N+1) loss values of (N+1) loss functions, N loss functions among the (N+1) loss functions correspond to the N second classifiers respectively, and a remaining one among the (N+1) loss functions corresponds to the first classifier.

19. The system for medical image interpretation according to claim 11, wherein the processor is further configured to:
    input one of the N feature maps to one of the N second classifiers so that the one of the N second classifiers outputs one of the N symptom interpretation results.

20. The system for medical image interpretation according to claim 11, wherein the convolutional neural network model further comprises a symptom feature extraction part, the symptom feature extraction part comprises at least one convolutional layer, and the processor is further configured to:
    input one of the N feature maps to the symptom feature extraction part for obtaining at least one symptom feature map; and
    input the at least one symptom feature map to one of the N second classifiers so that the one of the N second classifiers outputs one of the N symptom interpretation results.

* * * * *